United States Patent [19]

Yoshida et al.

[11] 4,321,409

[45] Mar. 23, 1982

[54] PROCESS FOR PRODUCING CONJUGATED DIENE MONOESTERS

[75] Inventors: Yoshinori Yoshida; Hironobu Shinohara, both of Yokohama, Japan

[73] Assignee: Japan Synthetic Rubber Co., Ltd., Tokyo, Japan

[21] Appl. No.: 103,477

[22] Filed: Dec. 14, 1979

[30] Foreign Application Priority Data

Jan. 17, 1979 [JP] Japan .................................. 54-2916

[51] Int. Cl.$^3$ ............................................ C07C 67/055
[52] U.S. Cl. ....................................... 560/244; 560/1; 560/113; 252/437; 252/439; 252/441
[58] Field of Search .......................... 560/244, 113, 1; 260/410.9 N

[56] References Cited

U.S. PATENT DOCUMENTS

| 3,671,577 | 6/1972 | Ono | 560/244 |
| 3,872,163 | 3/1975 | Shimizu | 560/244 |
| 4,131,743 | 12/1978 | Yoshida | 560/244 |

FOREIGN PATENT DOCUMENTS 2707096  8/1977  Fed. Rep. of Germany ...... 560/244
47-31919 11/1972 Japan .................................. 560/244

*Primary Examiner*—Natalie Trousof
*Assistant Examiner*—Michael Shippen
*Attorney, Agent, or Firm*—Oblon, Fisher, Spivak, McClelland & Maier

[57] ABSTRACT

A process for producing a conjugated diene monoester by reacting a gaseous mixture comprising a conjugated diene, a carboxylic acid and oxygen as reactive components, in which the fraction of said conjugated diene is preferably 12–60 mole % and the fraction of oxygen is preferably 5–30 mole %, in the gas phase in the presence of a catalyst, characterized by carrying out the reaction in the presence of a catalyst which comprises, as active components, (a) palladium, (b) at least one member selected from the group consisting of magnesium, calcium, barium, cerium, lanthanum, tungsten, copper, zinc, cadmium, boron, thallium, molybdenum, tin, lead, phosphorous, arsenic and selenium and (c) at least one alkali metal carboxylate, or a catalyst which comprises, as active components, these three components (a), (b) and (c) together with (d) at least one alkali metal halide.

22 Claims, No Drawings

PROCESS FOR PRODUCING CONJUGATED DIENE MONOESTERS

BACKGROUND OF THE INVENTION

1. Field of the Invention

This invention relates to a process for producing a conjugated diene monoester by reacting a conjugated diene, a carboxylic acid and oxygen by use of a novel catalyst.

2. Description of the Prior Art

Hitherto, a variety of processes have been proposed for producing unsaturated diesters by reacting a conjugated diene, a carboxylic acid and oxygen in the gas phase in the presence of a catalyst comprising palladium as main component. However, no satisfactory process has ever been reported concerning the process for selectively producing a monoester of conjugated diene as the main product. That is, as examples of the known processes for producing 1-acetoxy-1,3-butadiene, the process in which crotonaldehyde and acetic anhydride are the starting materials (Can. J. of Chem., 38, 1070 (1960)) and the process in which butadiene, acetic acid and oxygen are reacted in the presence of a solid catalyst comprising palladium and potassium acetate as active components (Japanese Patent Publication No. 48,927/74) have been proposed. However, the former process has a fault that the starting materials are difficult to obtain on an industrial scale, and the latter process has a fault that the main product is 1,4-diacetoxybutene-2 and 1-acetoxy-1,3-butadiene is obtained only as a by-product, so that its selectivity is low and its yield is quite low.

The present inventors previously discovered and disclosed in Japanese Patent Application Kokai (Laid-Open) No. 90,210/78 a catalyst comprising as active components (a) palladium, (b) at least one metal selected from the group consisting of aluminum, niobium, tantalum and zirconium, (c) at least one alkali metal halide, and (d) at least one alkali metal carboxylate, as a catalyst for producing a conjugated diene monoester with a high selectivity in a high yield, over a long period of time. The present inventors have further conducted extensive research thereon to find that a conjugated diene monoester can be obtained with a high selectivity in a high yield by using palladium in combination with at least one member selected from the group consisting of magnesium, calcium, barium, cerium, lanthanum, tungsten, copper, zinc, cadmium, boron, thallium, molybdenum, tin, lead, phosphorus, arsenic and selenium and at least one alkali metal carboxylate, as co-catalyst components. It has also been found that combustion reaction can be suppressed and, in addition, a stable catalytic activity can be obtained over a long period of time by further adding an alkali metal halide to the above-mentioned catalyst.

SUMMARY OF THE INVENTION

Thus, it is an object of this invention to provide a process for producing a conjugated diene monoester with a high selectivity in a high yield.

It is another object of this invention to provide a process for producing a conjugated diene monoester with suppressed combustion reaction.

It is a further object of this invention to provide a catalyst for producing a conjugated diene monoester which has a stable activity over a long period of time.

Other objects and advantages of this invention will become apparent from the following description.

According to this invention, there is provided a process for producing a conjugated diene monoester by reacting a gaseous mixture comprising, as reactive components, a conjugated diene, a carboxylic acid and oxygen in the gas phase in the presence of a catalyst, characterized by carrying out the reaction in the presence of a catalyst comprising, as active components, (a) palladium, (b) at least one member selected from the group consisting of magnesium, calcium, barium, cerium, lanthanum, tungsten, copper, zinc, cadmium, boron, thallium, molybdenum, tin, lead, phosphorus, arsenic and selenium and (c) at least one alkali metal carboxylate or a catalyst comprising, as active components, the above-mentioned three components (a), (b) and (c) together with (d) at least one alkali metal halide.

DETAILED DESCRIPTION OF THE INVENTION

In this invention, when butadiene is used as the conjugated diene and acetic acid is used as the carboxylic acid, there is obtained polymerizable 1-acetoxy-1,3-butadiene as the main product.

This 1-acetoxy-1,3-butadiene is also an intermediate for 1,4-diacetoxybutene-2, which can in turn be converted into 1,4-butanediol by hydrogenation followed by hydrolysis. This 1,4-butanediol is useful as a starting material for tetrahydrofuran, pyrrolidone, γ-butyrolactone and the like or as a starting material for polyesters.

This invention provides an industrially advantageous process for producing a conjugated diene monoester which is useful as mentioned above, and particularly a conjugated diene monoester which has one acyloxy group at the terminal of the conjugated double bond of the conjugated diene.

The conjugated dienes usable in this invention include butadiene and butadiene derivatives given by replacing at least one hydrogen atom of butadiene with a hydrocarbon residue, such as isoprene, 2,3-dimethylbutadiene, piperylene and the like. They can be selected from the group represented by the general formula (I):

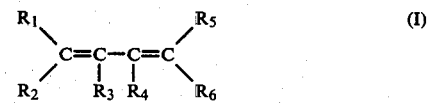

wherein $R_1$ to $R_6$ are independently hydrogen atoms or hydrocarbon residues, preferably alkyl groups, and at least one of $R_1$, $R_2$, $R_5$ and $R_6$ is a hydrogen atom. The number of carbon atoms of the above-mentioned hydrocarbon residue is preferably 6 or less, though it is not critical.

Further, said conjugated diene may also be selected from the group consisting of cyclic conjugated dienes such as cyclopentadine, alkylcyclopentadienes and cyclohexadiene. Among these conjugated dienes, particularly preferable are butadiene and isoprene. Said conjugated diene may not necessarily be pure but it may contain other hydrocarbons so long as they do not disturb the reaction.

The carboxylic acid used in this invention may be selected appropriately from aliphatic, alicyclic and aromatic carboxylic acids and the like. From an industrial point of view, lower aliphatic carboxylic acids such as acetic acid, propionic acid, butyric acid and the like are preferable. When butadiene is used as said conjugated diene and acetic acid is used as said carboxylic acid, the reaction is considered to proceed predominantly according to the following scheme (II):

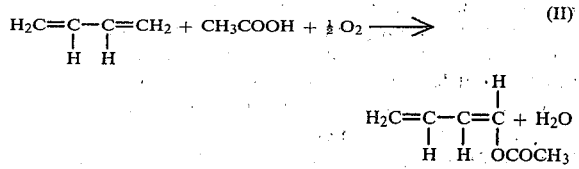

By this reaction, butadienyl-1-acetate in which an acetoxy group is attached to one terminal position of the conjugated double bond of butadiene is obtained as the main product and butadienyl-2-acetate and/or 1,4-diacetoxybutene-2 are obtained as by-products. In any case, however, the yield of these by-products is quite low.

The oxygen used as an oxidizing agent may not necessarily be pure oxygen, and it may be diluted with an inert gas such as nitrogen or carbon dioxide gas. Particularly, air can be used as an advantageous oxygen source because of its inexpensiveness.

The method for the preparation of the catalyst is not particularly limited, and any known method for the preparation of metallic catalysts supported on a carrier may be utilized appropriately. For example, a compound of palladium, i.e., component (a), and a compound of at least one of the specified members as component (b) are dissolved in an appropriate solvent; a carrier is introduced into the resulting solution, and the solvent is removed by distillation to attach the said compounds onto the carrier. Subsequently, the product is thoroughly dried by treating it in an atmosphere of an inert gas, such as nitrogen, carbon dioxide, helium or the like, at a temperature of 100° to 400° C. for 0.5 hour or more. Subsequently, it is reduced in a gaseous stream of hydrogen or a reductive organic compound, or it is reduced with a known reducing agent such as hydrazine, formaldehyde or the like. Subsequently, the above-mentioned carrier is introduced into an aqueous solution obtained by dissolving at least one alkali metal carboxylate (c), optionally together with at least one alkali metal halide (d), in water, and the water is removed by distillation to attach these components onto the carrier, whereby a catalyst can be prepared. The above-mentioned method for preparing the catalyst is no more than an example, and various modifications thereof can be made. As the carrier for the preparation of the catalyst, there may be used any conventional carrier for catalyst. Typical examples of the carrier include alumina, silica-alumina, silica, active charcoal, magnesia, diatomaceous earth, Carborundum, titania, zirconia and the like, among which alumina and silica-alumina are preferable in view of high activity which they can give.

Though the palladium compound used for the preparation of catalyst is not particularly limited, preferable are a palladium halide such as palladium chloride, an organic acid salt such as palladium acetate, an inorganic compound such as palladium nitrate, palladium oxide and palladium sulfate, or the like.

Though the concentration of palladium on carrier may be varied in a wide range, it is preferable to select the concentration appropriately from the range of from 0.1 to 10% by weight. However, the reaction can also proceed even at a concentration of less than 0.1% by weight or more than 10% by weight.

The source of the component (b), i.e., magnesium, calcium, barium, cerium, lanthanum, tungsten, copper, zinc, cadmium, boron, thallium, molybdenum, tin, lead, phosphorus, arsenic and selenium (zinc and selenium are preferable) is not particularly limited, but it may be such a compound as halide, organic acid salt, oxide, sulfide, nitrate, $\beta$-diketone complex salt or the like of said component (b), or it may be the component (b) per se.

The ratio of the component (b) to the palladium of component (a) in the catalyst is usually 0.01–20 gram-atoms, preferably 0.1–10 gram-atom, per gram-atom of palladium. The component (b) may also be used in combination of two or more.

As the alkali metal carboxylate of component (c), salts formed between alkali metals such as lithium, sodium, potassium and cesium and carboxylic acids such as formic acid, acetic acid, propionic acid, butyric acid, valeric acid and the like may be used, though among these components, salts of potassium and cesium are preferable. It is more preferable to use a salt of said alkali metal with the same carboxylic acid as used in the reaction. Preferably, component (c) is added to the catalyst after the reduction treatment. The amount thereof is usually 0.01 to 10 moles, preferably 0.05 to 5 moles, per 100 g of the carrier.

The alkali metal halides of component (d) include halides, i.e. fluoride, chloride, bromide and iodide, of alkali metals such as lithium, sodium, potassium, rubidium and cesium. Among these compounds, preferable are potassium fluoride, rubidium fluoride, cesium fluoride, sodium chloride, potassium chloride, rubidium chloride, cesium chloride, and cesium bromide. Cesium chloride is particularly preferred. The alkali metal halides of component (d) may also be used in combination of two or more. The amount of component (d) used is usually 10 moles or less, preferably 0.05 to 5 moles, per 100 g of the carrier.

In practising this invention, any appropriate reaction method such as fixed bed reaction method, fluidized bed reaction method and the like may be employed.

In practising the process of this invention, the temperature and pressure for the reaction are not critical. However, the reaction temperature is usually 100° to 300° C., preferably 100° to 200° C. The reaction may be effected either at atmospheric pressure or under pressure so far as the starting gas and the formed gas can be retained in the gaseous state.

In this invention, the molar fractions of the conjugated diene, the carboxylic acid and oxygen in the gaseous mixture may be selected freely. However, a gaseous mixture containing 12 to 60 mole% of the conjugated diene and 5 to 30 mole% of oxygen is particularly preferable. If the molar fraction of the conjugated diene is less than 12%, the yield of the conjugated diene monoester is low and the selectivity decreases due to the increased yield of unsaturated diester. If the molar fraction of the conjugated diene is more than 60 mole%, the activity decreases markedly with the lapse of time.

If the concentration of oxygen is less than 5 mole%, the yield is low. If it is more than 30 mole%, carbon dioxide is markedly formed so that the selectivity for the intended conjugated diene monoester drops.

Among the various cases mentioned above, cases in which the molar fraction of the conjugated diene is 18 to 50% and the molar fraction of oxygen is 10 to 25% are particularly preferable, the balance being the carboxylic acid. If necessary, it is also allowable to incorporate an inert gas such as nitrogen, steam or the like appropriately as a diluent.

DESCRIPTION OF THE PREFERRED EMBODIMENTS

This invention will be explained more specifically below with reference to Examples, which are not limitative but merely illustrative.

In the following Examples, the products were quantitatively analyzed by means of a gas chromatography. The percentages for selectivity are mole% while the other percentages are by weight unless otherwise specified.

EXAMPLES 1 TO 17

A solution was prepared by dissolving 0.334 g of anhydrous palladium chloride together with compound (A) (The name of compound (A) is shown in Table; the amount of the component (b) was fixed at 2 mg-equivalents throughout all the runs) in 20 ml of dilute hydrochloric acid having a concentration of 10%. Thereto was added 20 g of globular silica-alumina which had previously been calcined at 1,200° C. for 3 hours (particle diameter 4–6 mm, silica content 10%). The mixture was evaporated to dryness to support the above-mentioned compounds onto the silica-alumina. It was dried at 200° C. for 2 hours while allowing a stream of nitrogen to flow at a rate of 500 cc/minute. Subsequently, the compounds supported on the silica-alumina were reduced first at 200° C. for 2 hours and then at 400° C. for 2 hours, while passing hydrogen gas thereover at a rate of 100 cc/minute.

Then it was dipped for 20 hours in a solution of 2.000 g of potassium acetate in 30 ml of water, after which the excessive aqueous solution was removed and the residue was dried at 90° C. for 2 hours under reduced pressure to obtain a catalyst. A tubular flow reactor made of heat-resisting glass and having an inner diameter of 20 mm was packed with 10 ml of the catalyst thus obtained. A gaseous mixture comprising butadiene, acetic acid, oxygen and nitrogen (butadiene : acetic acid:oxygen:nitrogen=30:20:10:40 by volume) was introduced thereinto at a rate of 10 liters/hour and reaction was effected therein at 150° C. The results obtained are shown in Table 1.

EXAMPLES 18 TO 22

A catalyst was prepared by repeating the procedure of Example 1, except that the aqueous solution used was prepared by dissolving 3.367 g of cesium chloride and 2.000 g of potassium acetate in 30 ml of water. The same reaction as in Example 1 was carried out by the use of this catalyst. The results obtained are shown in Table 1.

COMPARATIVE EXAMPLE 1

A catalyst was prepared by repeating the procedure of Example 1, except that the compound (A) was not used. The same reaction as in Example 1 was carried out by use of this catalyst. The results obtained are shown in Table 1.

EXAMPLE 23

A catalyst was prepared by repeating the procedure of Example 18, except that 3.367 g of cesium chloride was replaced by 0.580 g of potassium fluoride. The same reaction as in Example 1 was carried out by use of this catalyst. The results obtained are shown in Table 1.

TABLE 1

| | Compound (A) as component (b) | Other catalyst components Kind | Amount (mmole/g of carrier) | Reaction time (hrs) | Space time yield of 1-acetoxy-butadiene (mmoles/liter-cat. · hr) | Selectivity for 1-acetoxy-butadiene (%) | Selectivity for di-acetoxy-butene (%) | Selectivity for $CO_2$ (%) |
|---|---|---|---|---|---|---|---|---|
| Example 1 | $MgCl_2$ | KOAc | 1 | 10 | 423.5 | 87.6 | 9.3 | 3.1 |
| | | | | 100 | 287.6 | 88.5 | 8.2 | 3.3 |
| Example 2 | $CaCl_2$ | KOAc | 1 | 10 | 418.4 | 87.9 | 8.9 | 3.2 |
| Example 3 | $BaCl_2$ | KOAc | 1 | 10 | 496.5 | 88.6 | 8.3 | 3.1 |
| Example 4 | $CeCl_3$ | KOAc | 1 | 10 | 384.9 | 86.3 | 10.7 | 3.0 |
| Example 5 | $LaCl_3$ | KOAc | 1 | 10 | 431.0 | 87.0 | 10.0 | 3.0 |
| | | | | 100 | 302.0 | 88.1 | 8.9 | 3.0 |
| Example 6 | $H_2WO_4$ | KOAc | 1 | 10 | 427.1 | 84.1 | 12.7 | 3.2 |
| Example 7 | $CuCl_2$ | KOAc | 1 | 10 | 401.1 | 86.3 | 10.7 | 3.0 |
| Example 8 | $ZnCl_2$ | KOAc | 1 | 10 | 572.2 | 89.1 | 7.9 | 3.0 |
| | | | | 100 | 396.3 | 90.5 | 6.4 | 3.1 |
| Example 9 | $CdCl_2$ | KOAc | 1 | 10 | 319.9 | 82.7 | 14.0 | 3.3 |
| Example 10 | $H_3BO_3$ | KOAc | 1 | 10 | 471.2 | 85.4 | 11.5 | 3.1 |
| Example 11 | $TlCl_3$ | KOAc | 1 | 10 | 235.7 | 80.3 | 16.8 | 2.9 |
| Example 12 | $H_2MoO_4$ | KOAc | 1 | 10 | 389.9 | 85.2 | 12.0 | 2.8 |
| | | | | 100 | 307.7 | 87.3 | 9.8 | 2.9 |
| Example 13 | $SnCl_2$ | KOAc | 1 | 10 | 427.7 | 93.9 | 3.2 | 2.9 |
| Example 14 | $PbCl_2$ | KOAc | 1 | 10 | 478.7 | 86.5 | 10.4 | 3.1 |
| Example 15 | $H_3PO_3$ | KOAc | 1 | 10 | 245.9 | 83.3 | 13.7 | 3.0 |
| Example 16 | $As_2O_3$ | KOAc | 1 | 10 | 423.6 | 91.3 | 5.8 | 2.9 |
| Example 17 | $SeO_2$ | KOAc | 1 | 10 | 602.1 | 90.9 | 6.3 | 2.8 |
| | | | | 100 | 499.9 | 91.5 | 5.6 | 2.9 |
| Example 18 | $MgCl_2$ | KOAc | 1 | 10 | 485.3 | 88.2 | 9.8 | 2.0 |
| | | CsCl | 1 | 100 | 407.7 | 88.7 | 9.2 | 2.1 |
| Example 19 | $LaCl_2$ | KOAc | 1 | 10 | 444.4 | 88.7 | 9.3 | 2.0 |
| | | CsCl | 1 | 100 | 401.9 | 89.2 | 8.8 | 2.0 |
| Example 20 | $ZnCl_2$ | KOAc | 1 | 10 | 633.3 | 91.3 | 6.8 | 1.9 |
| | | CsCl | 1 | 100 | 605.1 | 91.6 | 6.4 | 2.0 |
| Example 21 | $H_2MoO_4$ | KOAc | 1 | 10 | 423.5 | 88.3 | 9.6 | 2.1 |
| | | CsCl | 1 | 100 | 397.1 | 89.1 | 8.7 | 2.2 |
| Example 22 | $SeO_2$ | KOAc | 1 | 10 | 721.1 | 93.1 | 5.1 | 1.8 |

TABLE 1-continued

| | Compound (A) as component (b) | Other catalyst components | | Reaction time (hrs) | Space time yield of 1-acetoxy-butadiene (mmoles/liter-cat. · hr) | Selectivity for 1-acetoxy-butadiene (%) | Selectivity for di-acetoxy-butene (%) | Selectivity for $CO_2$ (%) |
|---|---|---|---|---|---|---|---|---|
| | | Kind | Amount (mmole/g of carrier) | | | | | |
| Comparative | | CsCl | 1 | 100 | 699.9 | 92.9 | 5.2 | 1.9 |
| Example 1 | — | KOAc | 1 | 10 | 43.3 | 57.2 | 39.4 | 3.4 |
| Example 23 | $MgCl_2$ | KOAc | 1 | 10 | 665.5 | 88.2 | 9.3 | 2.5 |
| | | KF | 1 | 100 | 495.1 | 88.7 | 8.9 | 2.4 |

EXAMPLES 24 TO 27

Reaction was carried out in the same manner as in Example 1, except that the composition of gaseous mixture was varied as shown in Table 2. The results obtained are shown in Table 2.

TABLE 2

| | Butadiene:Acetic acid:Oxygen:Nitrogen (molar ratio) | Reaction time (hr) | Space time yield of 1-acetoxy-butadiene (mmoles/liter-cat. · hr) | Selectivity for 1-acetoxy-butadiene (%) | Selectivity for di-acetoxy-butene (%) | Selectivity for $CO_2$ (%) |
|---|---|---|---|---|---|---|
| Example 24 | 30:20:3:47 | 10 | 222.7 | 87.7 | 9.3 | 3.0 |
| | | 100 | 199.7 | 88.3 | 8.7 | 3.0 |
| Example 25 | 30:20:50 | 10 | 538.2 | 83.9 | 6.3 | 9.8 |
| | | 100 | 139.6 | 81.6 | 8.3 | 10.1 |
| Example 26 | 70:20:10 | 10 | 497.3 | 89.3 | 7.7 | 3.0 |
| | | 100 | 112.5 | 82.5 | 12.2 | 5.3 |
| Example 27 | 5:20:10:65 | 10 | 203.1 | 88.5 | 8.4 | 3.1 |
| | | 100 | 187.6 | 88.6 | 8.2 | 3.2 |

EXAMPLE 28

The same procedure as in Example 1 was repeated, except that cesium acetate (1 mmole/g of carrier) was substituted for the potassium acetate, to obtain the result shown in Table 3.

EXAMPLE 29

The same procedure as in Example 1 was repeated, except that sodium acetate (1 mmole/g of carrier) was substituted for the potassium acetate, to obtain the result shown in Table 3.

EXAMPLE 30

The same procedure as in Example 23 was repeated, except that potassium chloride (1 mmole/g of carrier) was substituted for the potassium fluoride, to obtain the result shown in Table 3.

EXAMPLE 31

The same procedure as in Example 23 was repeated, except that sodium bromide (1 mmole/g of carrier) was substituted for the potassium fluoride, to obtain the result shown in Table 3.

TABLE 3

| | Compound (A) as component (b) | Other catalyst components | | Reaction time (hrs) | Space time yield of 1-acetoxy-butadiene (mmoles/liter-cat. · hr) | Selectivity for 1-acetoxy-butadiene (%) | Selectivity for di-acetoxy-butene (%) | Selectivity for $CO_2$ (%) |
|---|---|---|---|---|---|---|---|---|
| | | Kind | Amount (mmole/g of carrier) | | | | | |
| Example 28 | $MgCl_2$ | CsOAc | 1 | 10 | 538.6 | 89.1 | 7.8 | 3.1 |
| | | | | 100 | 416.2 | 89.2 | 7.5 | 3.3 |
| Example 29 | $MgCl_2$ | NaOAc | 1 | 10 | 383.5 | 87.1 | 9.6 | 3.3 |
| | | | | 100 | 258.1 | 87.3 | 9.3 | 3.4 |
| Example 30 | $MgCl_2$ | KOAc | 1 | 10 | 462.3 | 89.1 | 8.9 | 2.0 |
| | | KCl | 1 | 100 | 400.3 | 89.5 | 8.4 | 2.1 |
| Example 31 | $MgCl_2$ | KOAc | 1 | 10 | 427.3 | 88.8 | 8.9 | 2.3 |
| | | NaBr | 1 | 100 | 345.1 | 89.3 | 8.4 | 2.3 |

We claim:

1. In a process for producing a conjugated diene monoester by reacting a gaseous mixture comprising, as the reactive components, a conjugated diene, a carboxylic acid and oxygen in the gas phase in the presence of a catalyst, the improvement which comprises carrying out the reaction in the presence of a catalyst prepared by supporting on a carrier (a) a palladium compound and (b) a compound or element of at least one member selected from the group consisting of magnesium, calcium, barium, cerium, lanthanum, tungsten copper, zinc, cadmium, boron, thallium, molybdenum, tin, lead, phosphorous, arsenic and selenium, reducing the so-supported components, and then adding thereto (c) at least one alkali metal carboxylate and (d) at least one alkali metal halide in an amount of 0.05 to 5 moles per 100 g of the carrier.

2. A process according to claim 1, wherein the fraction of the conjugated diene in the gaseous mixture is 12–60 mole% and the fraction of oxygen is 5–30 mole%.

3. A process according to claim 1 or 2, wherein said conjugated diene is a compound represented by the following formula:

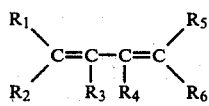

wherein $R_1$–$R_6$ are independently hydrogen atoms or hydrocarbon residues, and at least one of $R_1$, $R_2$, $R_5$ and $R_6$ is a hydrogen atom.

4. A process according to claim 1 or 2, wherein said conjugated diene is butadiene or isoprene.

5. A process according to claim 1 or 2, wherein said carboxylic acid is a lower aliphatic carboxylic acid.

6. A process according to claim 5, wherein said lower aliphatic carboxylic acid is acetic acid, propionic acid or butyric acid.

7. A process according to claim 5, wherein said lower aliphatic carboxylic acid is acetic acid.

8. A process according to claim 4, wherein said carboxylic acid is acetic acid.

9. A process according to claim 1, wherein said carrier is alumina, silica-alumina, silica, active charcoal, magnesia, diatomaceous earth, Carborundum, titania or zirconia.

10. A process according to claim 1, 2 or 9, wherein the ratio of (b) to (a) is 0.01 to 20 gram-atoms per gram-atom of palladium and wherein (b) is at least one element selected from the group consisting of magnesium, calcium, barium, cerium, lanthanum, tungsten, copper, zinc, cadmium, boron, thallium, molybdenum, tin, lead, phosphorous, arsenic and selenium.

11. A process according to claim 1, 2 or 9, wherein the ratio of (b) to (a) is 0.1 to 10 gram-atoms per gram-atom of palladium and wherein (b) is at least one element selected from the group consisting of magnesium, calcium, barium, cerium, lanthanum, tungsten, copper, zinc, cadmium, boron, thallium, molybdenum, tin, lead, phosphorous, arsenic and selenium.

12. A process according to claim 1, wherein the component (b) is a zinc or selenium compound.

13. A process according to claim 1, 2 or 9, wherein said component (c) is an alkali metal salt of formic, acetic, propionic, butyric, or valeric acid.

14. A process according to claim 12, wherein the alkali metal of component (c) is lithium, sodium, potassium or cesium.

15. A process according to claim 13, wherein the alkali metal of component (c) is potassium or cesium.

16. A process according to claim 7, wherein said component (c) is potassium acetate or cesium acetate.

17. A process according to claim 9, wherein the proportion of component (c) is 0.01 to 10 moles per 100 g of the carrier.

18. A process according to claim 1, 2 or 9, wherein said component (d) is a fluoride, chloride, bromide or iodide of lithium, sodium, potassium, rubidium or cesium.

19. A process according to claim 15, wherein said component (d) is potassium fluoride, rubidium fluoride, cesium fluoride, sodium chloride, potassium chloride, rubudium chloride, cesium chloride or cesium bromide.

20. A process according to claim 9, wherein the proportion of component (d) is 10 moles or less per 100 g of the carrier.

21. A process according to claim 1, 2 or 9, wherein the reaction temperature is 100° C. to 300° C.

22. A process according to claim 21, wherein the reaction is effected at atmospheric pressure or under pressure.